US007807604B2

(12) United States Patent
Strebelle et al.

(10) Patent No.: US 7,807,604 B2
(45) Date of Patent: Oct. 5, 2010

(54) OXYCHLORINATION CATALYST AND PROCESS USING SUCH A CATALYST

(75) Inventors: Michel Strebelle, Brussels (BE); André Petitjean, Brussels (BE)

(73) Assignee: Solvay (Societe Anonyme), Brussels (BE)

( * ) Notice: Subject to any disclaimer, the term of this patent is extended or adjusted under 35 U.S.C. 154(b) by 0 days.

(21) Appl. No.: 11/914,048

(22) PCT Filed: May 12, 2005

(86) PCT No.: PCT/EP2005/052190

§ 371 (c)(1),
(2), (4) Date: Feb. 15, 2008

(87) PCT Pub. No.: WO2006/119804

PCT Pub. Date: Nov. 16, 2006

(65) Prior Publication Data

US 2008/0214879 A1    Sep. 4, 2008

(51) Int. Cl.
*B01J 23/72* (2006.01)
*B01J 21/04* (2006.01)
*B01J 23/78* (2006.01)
*C07C 17/013* (2006.01)

(52) U.S. Cl. ........................ 502/346; 502/325; 502/326; 502/327; 502/328; 502/330; 502/331; 502/332; 502/333; 502/334; 502/339; 502/340; 502/341; 502/344; 502/345; 570/224; 570/243

(58) Field of Classification Search ......... 502/325–334, 502/344–348, 339–341; 570/224, 243
See application file for complete search history.

(56) References Cited

U.S. PATENT DOCUMENTS

| 4,451,683 A * | 5/1984 | Davies et al. ............... 570/224 |
| 4,910,354 A | 3/1990 | Derleth et al. |
| 5,055,019 A | 10/1991 | Meyer et al. |
| 5,260,247 A | 11/1993 | Helmut et al. |
| 6,803,342 B1 | 10/2004 | Derleth et al. |
| 2002/0007097 A1 | 1/2002 | Walsdorff et al. |
| 2007/0142682 A1 | 6/2007 | Strebelle et al. |
| 2007/0161830 A1 | 7/2007 | Strebelle |

FOREIGN PATENT DOCUMENTS

| EP | 1 155 740 | 11/2001 |
| WO | 2005/046866 | 5/2005 |

OTHER PUBLICATIONS

Noweck, Klaus, "Fatty Alcohols", Ullmann's Encyclopedia of Industrial Chemistry, 2001.
U.S. Appl. No. 11/719,652, filed May 18, 2007, Strebelle, et al.
U.S. Appl. No. 11/815,505, filed Aug. 3, 2007, Strebelle, et al.
PURALOX®/CATALOX® High purity activated aluminas—Brochure by Sasol GmbH—Jan. 1, 2003.
Table annexed to Condea Chemie brochure entitled High purity activated aluminas PURALOX®/CATALOX®—Oct. 1999.

* cited by examiner

*Primary Examiner*—Timothy C Vanoy
*Assistant Examiner*—Diana J Liao
(74) *Attorney, Agent, or Firm*—Oblon, Spivak, McClelland, Maier & Neustadt, L.L.P.

(57) ABSTRACT

Oxychlorination catalyst containing at least copper as an active element deposited on a support characterized in that the support consists essentially of an alumina obtained by calcination of an alumina hydrate obtained as by-product of the ALFOL® linear primary alcohol process and use of such catalyst in an oxychlorination process of a hydrocarbon containing 1 to 4 carbon atoms.

20 Claims, No Drawings

OXYCHLORINATION CATALYST AND PROCESS USING SUCH A CATALYST

This application is a 371 of PCT/EP05/52190, filed May 12, 2005.

The present invention relates to an oxychlorination catalyst, to an alumina and to an oxychlorination process using such a catalyst.

Oxychlorination reactions generally make use of catalyst containing active elements deposited on an inert support. These supports include alumina, silica gels, mixed oxides and clays or other supports of natural origin.

In the particular case of oxychlorination reactions of hydrocarbons and particularly of ethylene, using hydrogen chloride and air, or oxygen, catalysts containing active elements including copper deposited on an inert support like alumina have been very successful.

Several processes for the preparation of alumina are known. One of them is the Bayer process which allows the preparation of alumina from bauxite which presents the disadvantage of containing relatively high level of alkali metals.

Other processes for the preparation of alumina are the processes for the production of synthetic fatty alcohols using organic aluminum compounds starting from aluminum metal and based on the work of Prof. Dr. Ziegler leading to the formation of high purity alumina hydrate as by-product. An example of such last-mentioned processes is the process called ALFOL® process using the Ziegler process to obtain an intermediate aluminum alkoxide. The ALFOL® process is usually coupled with another process recycling the obtained alcohols to convert aluminum metal to aluminum alkoxide not using the Ziegler reaction ("Tonerde-Aus-Metall" or TAM process), both of them leading to the formation of high purity alumina hydrate as by-product of the hydrolysis of the aluminum alkoxide to a mixture of linear primary alcohols. The TAM process as detailed above may also be used as stand-alone process for the preparation of alumina.

High purity alumina hydrate commercially available are classically prepared by a combination of the ALFOL® process and of the TAM process, notably by Sasol, previously Condea. Such commercial high purity alumina hydrate are sold by Sasol under the trade name PURAL®.

Disadvantageously, we have observed in oxychlorination catalysts that the carefully adjusted content of the active elements deposited on a support can shift by itself during the industrial use of the catalyst if the support is an alumina obtained from alumina hydrate prepared as by-product of the combined ALFOL®/TAM process or prepared by the TAM process alone. Troubles as poor fluidization pattern or reduced activity have been observed with aged, unstable catalysts. This must lead to discard the catalyst and to replace the loading by a fresh one. The analysis of the used catalyst has shown an unforeseen phenomenon of an apparent increase of the concentration of some active elements in the catalyst during its industrial lifetime. For example, it has been observed in oxychlorination catalyst containing magnesium as active element (as magnesium chloride) that the magnesium concentration can be increasing from an initial value of 17 g/kg, expressed in metal form with respect to the total weight of dry catalyst, to values exceeding 20 µg and in some case reaching 30 g/kg within a period of time of more than one year. The explanation satisfying the mass balance law should be the progressive accumulation of magnesium and other active elements in some alumina particles and the loss by the fluid bed of less impregnated particles.

While the ALFOL® and TAM processes are very close processes, we have now very surprisingly found that such a phenomenon is not observed with an oxychlorination catalyst containing at least copper as active element, deposited on a support consisting essentially of an alumina obtained by calcination of an alumina hydrate obtained from the ALFOL® linear primary alcohol process. The active elements content of such a catalyst remains stable for more than one year of industrial use in the oxychlorination of ethylene to 1,2-dichloroethane.

Accordingly, the present invention relates to an oxychlorination catalyst containing at least copper as an active element deposited on a support wherein the support consists essentially of an alumina obtained by calcination of an alumina hydrate obtained as by-product of the ALFOL® linear primary alcohol process.

For the purposes of the present invention, alumina means a compound with the formula $Al_2O_3$ and alumina hydrate means a compound with the formula $AlO(OH)$ containing eventually some additional water in its structure.

The alumina hydrate is advantageously a boehmite.

The alumina used in the catalyst according to the invention further advantageously has a mean particle diameter between 5 and 200 µm, preferably between 20 and 120 µm. The mean particle diameter is preferably established by classifications measured on dry vibrating screens.

The specific surface area of the alumina measured by the BET method with nitrogen is advantageously between 50 $m^2/g$ and 300 $m^2/g$, preferably between 75 and 250 $m^2/g$ and in a particularly preferred manner between 100 $m^2/g$ and 210 $m^2/g$.

The pore volume of the alumina used in the catalyst according to the invention is advantageously between 0.1 and 1 $cm^3/g$, preferably between 0.2 and 0.8 $cm^3/g$ and in a particularly preferred manner between 0.25 and 0.6 $cm^3/g$.

Finally, the bulk density (measured by free flow) of the alumina used in the catalyst according to the invention advantageously varies between 0.5 and 1 $kg/dm^3$, preferably between 0.6 and 0.9 $kg/dm^3$ and in a particularly preferred manner between 0.65 and 0.75 $kg/dm^3$.

It should be noted that the alumina may contain typically at least 0.09, preferably at least 0.1, more preferably at least 0.115 wt % of titanium and typically at most 0.15, preferably at most 0.13, more preferably at most 0.11 wt % of titanium and possibly traces of carbon, alkali metals, silicon or iron that may have been introduced in one of the steps of the alumina hydrate production by the ALFOL® process. Alumina which contain from 0.09 to 0.11 wt % of titanium are particularly preferred. Others containing from 0.115 to 0.15 wt % of titanium are also particularly preferred.

By the wording "consisting essentially of", it is meant that the support either contains no other alumina apart from the one specified or only contains other alumina in an amount which has no tangible effect on the performance of the oxychlorination catalyst.

Advantageously, the support consists solely of the alumina obtained by calcination of an alumina hydrate obtained as by-product of the ALFOL® linear primary alcohol process. In other words, this means that the alumina used as support for preparing the oxychlorination catalyst according to the invention is advantageously coming exclusively from the ALFOL® process.

The ALFOL® linear primary alcohol process comprises advantageously the following steps:

A. hydrogenation of triethylaluminum in the presence of aluminum metal leading to hydrogenated diethylaluminum;
B. ethylation of hydrogenated diethylaluminum by adding ethylene leading to triethylaluminum;

C. growth reaction to build a mixture of higher molecular weight trialkylaluminums (called ethylene growth product) by further addition of ethylene to triethylaluminum;

D. oxidation of the ethylene growth product with air to the corresponding aluminum alkoxide; and E. hydrolysis of the aluminum alkoxide to a mixture of linear primary alcohols and an aqueous suspension of alumina hydrate.

Hydrogenation step A is advantageously realized in the presence of a solvent, at a temperature of approximately 135° C. and a pressure of approximately 7 MPa. The aluminum metal which is used is advantageously in the form of a powder.

Ethylation step B is advantageously realized at a temperature of approximately 120° C. and a pressure of approximately 2 MPa.

Growth reaction step C is advantageously conducted at moderate temperatures to minimize a competing displacement reaction that produces by-product olefins. Preferred temperature is about 120° C. The growth reaction is advantageously allowed to proceed until the alkyl chains in the ethylene growth product have grown to the required average length of carbon atoms. The distribution of chain lengths in the ethylene growth product and the alcohols derived from them usually conforms with the statistical distribution predicted by a Poisson curve. The pressure is advantageously approximately 12 MPa.

Oxidation step D is advantageously realized at a temperature of approximately 50° C. and a pressure of approximately 0.5 MPa.

Prior to hydrolysis step E, the solvent is advantageously removed by distillation. Hydrolysis step E is advantageously realized with water (neutral hydrolysis) at a temperature of approximately 90° C. and a pressure of approximately 0.1 MPa.

Preferably, after step E and before calcination, the aqueous suspension of alumina hydrate is spray-dried in order to obtain microspheres of alumina hydrate. The temperature at which the spray-drying is done is not critical. Advantageously, the gas used for the spray-drying is at a temperature of about 300 to 600° C., preferable of about 500 to 600° C. and the temperature at the output of the spray-dryer is about 100 to 250° C., preferably about 100 to 170° C.

The catalyst according to the invention is characterized in that calcination of alumina hydrate is operated at a temperature advantageously not less than 600, preferably not less than 650, more preferably not less than 700 and most preferably not less than 750° C. The temperature of the calcination is advantageously not more than 1100, preferably not more than 950, more preferably not more than 900 and most preferably not more that 850° C. Very good results have been obtained with a temperature of the calcination comprised between 750 and 850° C.

The calcination may be achieved by all means but is preferably carried out by using a rotary kiln with external heating.

For the purposes of the present invention, by active elements, it is meant elements i.e. metals in their elementary state, but also compounds of these elements (metals) active as oxychlorination catalysts, having a tangible effect on the course of the reaction excluding traces of compounds being present as inert impurities in the support or in the compounds used to impregnate this support or coming through external contamination.

The catalyst according to the invention contains at least copper as an active element deposited on a support. The catalyst according to the invention advantageously contains, in addition to copper, at least another active element selected from alkali metals, alkaline-earth metal, rare earth metals and metals of the group consisting of ruthenium, rhodium, palladium, osmium, iridium, platinum and gold.

Alkali metals means the elements of Group Ia of the Periodic Table. The preferred alkali metals include potassium, sodium, lithium and caesium.

Alkaline-earth metals means the elements of Group Ia of the Periodic Table. The preferred alkaline-earth metals include magnesium, calcium, barium and strontium. Magnesium is particularly preferred.

Rare earth metals means the elements 57 to 71 of the Periodic Table and mixtures thereof.

A preferred catalyst according to the invention contains, in addition to copper, at least one alkaline-earth metal, particularly magnesium.

A more preferred catalyst according to the invention contains, in addition to copper and at least one alkaline-earth metal, at least one active element selected from alkali metals, rare earth metals and metals of the group consisting of ruthenium rhodium, palladium, osmium, iridium, platinum and gold.

A most preferred catalyst according to the invention contains, in addition to copper and at least one alkaline-earth metal, at least one active element selected from alkali metals and rare earth metals.

A particularly most preferred catalyst according to the invention contains, as active elements, copper, magnesium, at least one alkali metal and possibly at least one rare earth metal.

Catalysts of which the active elements are copper, magnesium and at least one alkali metal yield good results.

Catalyst containing the following active elements yield very good results: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium, copper/magnesium/sodium/potassium, copper/magnesium/sodium/caesium and copper/magnesium/potassium/caesium.

Catalysts containing the following active elements yield excellent results: copper/magnesium/potassium, copper/magnesium/sodium; copper/magnesium/lithium, copper/magnesium/caesium, copper/magnesium/sodium/lithium, copper/magnesium/potassium/lithium and copper/magnesium/caesium/lithium.

The copper content, calculated in metal form, is advantageously between 30 and 90 g/kg, preferably between 40 and 75 g/kg and in a particularly preferred manner between 50 and 70 g/kg of catalyst.

The magnesium content, calculated in metal form, is advantageously between 10 and 30 g/kg, preferably between 12 and 25 g/kg and in a particularly preferred manner between 15 and 20 g/kg of catalyst.

The alkali metal(s) content, calculated in metal form, is advantageously between 0.1 and 30 g/kg, preferably between 0.5 and 20 g/kg and in a particularly preferred manner between 1 and 15 g/kg of catalyst.

The Cu:Mg:alkali metal(s) atomic ratios are normally 1:0.1-2:0.05-2, preferably 1:0.2-1.5:0.1-1.5 and in a particularly preferred manner 1:0.5-1:0.15-1.

The metals salts used to impregnate the alumina can be oxides, hydroxides, nitrates, carbonates, acetates, chlorides or any other salts able to be converted at least partially into chloride under the oxychlorination conditions. They are preferably chlorides.

The active elements of the catalyst according to the invention are advantageously present in the catalyst in the form of compounds of the metals e.g. oxides, hydroxides, nitrates, carbonates, acetates, chlorides or any compound able to be converted at least partially into chloride under the oxychlorination conditions. They are preferably in the form of chlorides.

The catalyst according to the invention advantageously has a specific surface area measured by the BET method with nitrogen between 25 m$^2$/g and 300 m$^2$/g, preferably between 50 and 200 m$^2$/g and in a particularly preferred manner between 75 and 175 m$^2$/g.

The method for obtaining the catalyst according to the invention is not critical in itself. A preferred preparation method consists in dry impregnating an alumina according to the invention with an aqueous solution containing the desired quantities of the metals salts. Various additives including hydrochloric acid can be added to the aqueous solution. The impregnation can be carried out in one or more steps. It is preferably carried out in a single step. The impregnation is in a particularly preferred manner followed by a step of drying of the catalyst obtained. By dry impregnation, it is meant an impregnation by pouring onto the alumina, a solution of the impregnation salts having a volume lower than the pore volume of the alumina which allows to reach a determined concentration of the active elements on the alumina after a drying stage. This method is preferred compared to the method consisting in soaking the alumina in the impregnation solution.

The impregnation is advantageously carried out at a temperature above ambient temperature to favour the solubility of the impregnating salts.

The appearance of a liquid phase not adsorbed by the solid is advantageously avoided by limiting the volume of the impregnating solution to 70 to 100% of the pore volume of the quantity of alumina employed.

The oxychlorination catalyst according to the invention is advantageously characterized by the fact that it remains stable in its active elements content during its industrial use in the oxychlorination of ethylene to 1,2-dichloroethane for more than one year—i.e. it does not show an apparent concentration increase for any of the active elements of more than 10%, preferably 5%, within a period of time of one year. More especially, when containing magnesium, the oxychlorination catalyst according to the invention does not show an apparent magnesium concentration increase of more than 10%, preferably 5%, most preferably 2.5% within a period of time of one year.

The catalyst according to the invention can be employed in any method involving an oxychlorination of a hydrocarbon containing 1 to 4 carbon atoms.

This is why the invention further relates to an oxychlorination process of a hydrocarbon containing 1 to 4 carbon atoms using the catalyst according to the invention.

The hydrocarbons containing 1 to 4 carbon atoms include methane, ethane, ethylene, propane, propylene, butenes, acetylene, chloroethane, chloropropane, dichloromethane, dichloroethane and other halogenated compound In a very particularly preferred manner, the oxychlorination is the oxychlorination of ethylene to 1,2-dichloroethane.

The oxychlorination reaction can take place in a fixed bed or a fluidized bed.

If the reaction takes place in a fixed bed, the catalyst according to the invention is preferably in the form of granules or pellets of any shape. If the reaction takes place in a fluidized bed, the catalyst according to the invention is preferably in powder form.

The oxychlorination reaction preferably takes place in a fluidized bed.

The molecular oxygen necessary for the oxychlorination reaction is advantageously introduced into the reactor, either diluted, for example in the form of air, or pure. The oxygen is preferably introduced pure into the reactor. By pure oxygen, it is meant oxygen of more than 99% purity, for example obtained by air distillation.

The temperature at which the oxychlorination reaction takes place is normally between 200 and 300° C., preferably between 220 and 280° C., in a particularly preferred manner between 230 and 270° C.

The pressure at which the oxychlorination reaction takes place is not critical in itself. Normally, it takes place at pressures between 0.1 and 1 MPa and preferably between 0.1 and 0.8 MPa.

The fluidizing rate of the catalyst according to the invention during the oxychlorination reaction is not critical in itself. Its choice essentially depends of the particle size distribution of the catalyst and the dimensions of the apparatus. In general, the operation takes place with fluidizing rates between 5 and 100 cm/s.

Finally, the ratio of the reactants employed for the oxychlorination reaction is the same as the one generally used in prior methods. Normally, the operation takes place with a slight excess of ethylene with respect to the stoichiometric quantity necessary to react with the HCl used. However, the catalyst according to the invention serves equally to operate with large excesses of ethylene or in the neighbourhood of stoichiometry, or indeed even with an excess of HCl.

The invention further relates to an alumina obtained by calcination at a temperature comprised between 700 and 950° C. of an alumina hydrate obtained as by-product of the ALFOL® linear primary alcohol process.

The preferred conditions for calcination are the same as those already described above for the catalyst according to the invention.

The invention further relates to the use of the catalyst according to the invention in an oxychlorination process for allowing the oxychlorination reaction, particularly of ethylene to 1,2-dichloroethane, taking place under optimal conditions avoiding catalyst degradation.

Accordingly, the present invention relates to the use in an oxychlorination process of the catalyst according to the invention for allowing stable operation conditions over a time period of more than one year for the oxychlorination reaction (no poor fluidization pattern or reduced activity).

Complementary to the fact that it remains stable in its active elements content during its industrial use, the catalyst according to the invention also presents the advantage of procuring a stable oxygen profile in the tail gases and hence in the recycled gases. This particular advantage is important from the standpoint of safety and control of an industrial reactor. Further, the catalyst according to the invention presents also the advantage of ensuring a stable ethylene content in these tail gases, which is an economic advantage. Finally, the catalyst according to the invention presents also the advantage of avoiding the deposition of soiling material on the surface of the bundle of tubes of the heat exchanger located in the reactor. This deposition limits heat exchange and capacity of the reactor when it occurs.

The following examples are intended to illustrate the invention without limiting its scope.

EXAMPLE 1

According to the Invention

A fresh catalyst containing as active elements, copper, magnesium, potassium and lithium was prepared from a hydrated alumina (boehmite) obtained exclusively by the ALFOL® process which was calcined at a temperature comprised between 750 and 850° C. using a rotary kiln with external heating to obtain an alumina with a specific surface area of 180 m$^2$/g.

This alumina exhibited the following other properties: pore volume=0.35 cm$^3$/g; bulk density (measured by free flow) 0.7 kg/dm$^3$, and mean particle diameter=47 µm.

To about 750 g of this alumina, an aqueous impregnation solution was added comprising, in the dissolved state, 162 g of $CuCl_2.2H_2O$, 144 g of $MgCl_2.6H_2O$, 17.2 g of KCl and 10.6 g of LiCl. The wet solid was then heated at 180° C. for 18 h.

1 kg of catalyst was thus obtained. The content of the different active elements of the catalyst was measured by inductively coupled plasma optic emission spectrometry (ICP-OES) after complete dissolution of the sample. This content, calculated in metal form in g per kg of the catalyst, is given in table I.

Expressed as an atomic ratio, the proportion of the various active elements metals Cu:Mg:K:Li was 1:0.74:0.24:0.26.

EXAMPLE 2

According to the Invention

About 16 tons of catalyst prepared by the method described in Example 1 were placed in an industrial fluidized bed reactor for the oxychlorination of ethylene to 1,2-dichloroethane.

After 11 months of operation at a temperature comprised between 240 and 255° C. and a pressure comprised between 0.4 and 0.6 MPa, a sample of the catalyst was extracted and analyzed. The content of the different active elements, calculated in metal form in g per kg of the catalyst, is given in table I.

EXAMPLE 3

According to the Invention

The oxychlorination reaction described in Example 2 was continued. A sample of the catalyst was extracted from the reactor 3 months after the first extraction detailed in Example 2 (i.e. after a total of 14 months of operation) and analyzed. The content of the different active elements, calculated in metal form in g per kg of the catalyst, is given in table I.

EXAMPLE 4

Comparative

A fresh catalyst containing as active elements, copper, magnesium, potassium and lithium was prepared from a hydrated alumina (boehmite) obtained exclusively by the TAM process which was calcined at a temperature comprised between 750 and 850° C. using a rotary kiln with external heating to obtain an alumina with a specific surface area of 180 m$^2$/g.

This alumina exhibited the following other properties: pore volume=0.35 cm$^3$/g; bulk density (measured by free flow) 0.7 kg/dm$^3$, and mean particle diameter=47 µm.

To about 750 g of this alumina, an aqueous impregnation solution was added comprising, in the dissolved state, 162 g of $CuCl_2.2H_2O$, 144 g of $MgCl_2.6H_2O$, 17.2 g of KCl and 10.6 g of LiCl. The wet solid was then heated at 180° C. for 18 h.

1 kg of catalyst was thus obtained. The content of the different active elements of the catalyst was measured by inductively coupled plasma optic emission spectrometry (ICP-OES) after complete dissolution of the sample. This content, calculated in metal form in g per kg of the catalyst, is given in table I.

Expressed as an atomic ratio, the proportion of the various active elements metals Cu:Mg:K:Li was 1:0.74:0.24:0.26.

EXAMPLE 5

Comparative

About 16 tons of catalyst prepared by the method described in Example 4 were placed in an industrial fluidized bed reactor for the oxychlorination of ethylene to 1,2-dichloroethane.

After 3.5 months of operation at a temperature comprised between 240 and 255° C. and a pressure comprised between 0.4 and 0.6 MPa, a sample of the catalyst was extracted and analyzed. The content of the different active elements, calculated in metal form in g per kg of the catalyst, is given in table I.

EXAMPLE 6

Comparative

A fresh catalyst containing as active elements, copper, magnesium, sodium and lithium was prepared from a hydrated alumina (boehmite) obtained by the combined ALFOL®/TAM process which was calcined at a temperature comprised between 750 and 850° C. using a rotary kiln with external heating to obtain an alumina with a specific surface area of 180 m$^2$/g.

This alumina exhibited the following other properties: pore volume=0.35 cm$^3$/g; bulk density (measured by free flow) 0.7 kg/dm$^3$, and mean particle diameter=47 µm.

To about 800 g of this alumina was added an aqueous impregnation solution comprising $CuCl_2.2H_2O$, $MgCl_2.6H_2O$, NaCl and LiCl in the appropriate amounts and proportions. The wet solid was then heated at 180° C. for 18 h.

1 kg of catalyst was thus obtained. The content of the different active elements of the catalyst was measured by inductively coupled plasma optic emission spectrometry (ICP-OES) after complete dissolution of the sample. This content, calculated in metal form in g per kg of the catalyst, is given in table I.

Expressed as an atomic ratio, the proportion of the various active elements metals Cu:Mg:Na:Li was 1:0.74:0.09:0.28.

EXAMPLE 7

Comparative

About 16 tons of catalyst prepared by the method described in Example 6 were placed in an industrial fluidized bed reactor for the oxychlorination of ethylene to 1,2-dichloroethane.

After more than 36 months of operation at a temperature comprised between 240 and 255° C. and a pressure comprised between 0.4 and 0.6 MPa, the oxychlorination had to be stopped as the catalyst presented an irregular fluidization pattern. A sample of the catalyst was analyzed. The content of the different active elements, calculated in metal form in g per kg of the catalyst, is given in table I. The results showed that the observed accumulation of active elements can lead to a production failure.

TABLE I

| Active elements | Content of the different active elements in the catalyst (g of metal form/kg of catalyst) | | | | | | |
|---|---|---|---|---|---|---|---|
| | Ex 1 Fresh catalyst | Ex 2 After 11 months | Ex 3 After 14 months | Ex 4 Fresh catalyst | Ex 5 After 3.5 months | Ex 6 Fresh catalyst | Ex 7 After >36 months |
| Cu | 60 | 60 | 60 | 60 | 67 | 60 | 86 |
| Mg | 17 | 17 | 17 | 17 | 19 | 17 | 38 |
| K | 9 | n.d. | n.d. | 9 | 9.3 | | |
| Li | 1.8 | 1.9 | 1.9 | 1.8 | 2.0 | 2 | 4.4 |
| Na | | | | | | 2 | 1.9 | n.d.: non determined

The invention claimed is:

1. An oxychlorination catalyst comprising at least copper as an active element deposited on a support, wherein the support consists essentially of an alumina obtained by calcination of an alumina hydrate obtained as a by-product of only the ALFOL® linear primary alcohol process,
   wherein the ALFOL® linear primary alcohol process comprises:
   A. hydrogenation of triethylaluminum in the presence of aluminum metal, leading to hydrogenated diethylaluminum;
   B. ethylation of the hydrogenated diethylaluminum by adding ethylene, leading to triethylaluminum;
   C. growth reaction to build a mixture of higher molecular weight trialkylaluminums (called ethylene growth product) by further addition of ethylene to the triethylaluminum;
   D. oxidation of the ethylene growth product with air to the corresponding aluminum alkoxide; and
   E. hydrolysis of the aluminum alkoxide to a mixture of linear primary alcohols and an aqueous suspension of alumina hydrate.

2. The catalyst according to claim 1, wherein the support consists solely of the alumina obtained by calcination of the alumina hydrate.

3. The catalyst according to claim 1, wherein the alumina hydrate is a boehmite.

4. The catalyst according to claim 1, wherein, after E and before calcination, the aqueous suspension of alumina hydrate is spray-dried in order to obtain microspheres of alumina hydrate.

5. The catalyst according to claim 1, wherein the calcination of alumina hydrate is operated at a temperature of not more than 950° C.

6. The catalyst according to claim 1, further comprising at least another active element selected from alkali metals, alkaline-earth metal, rare earth metals and metals of the group consisting of ruthenium, rhodium, palladium, osmium, iridium, platinum and gold.

7. The catalyst according to claim 1, further comprising at least one alkaline-earth metal.

8. The catalyst according to claim 7, further comprising at least one active element selected from alkali metals, rare earth metals and metals of the group consisting of ruthenium, rhodium, palladium, osmium, iridium, platinum and gold.

9. The catalyst according to claim 8, wherein the active elements are copper, magnesium and at least one alkali metal.

10. An oxychlorination catalyst according to claim 1, wherein the oxychlorination catalyst does not show an apparent concentration increase for any of the active elements therein of more than 10% after use in an oxychlorination reaction for a period of time of one year.

11. An process of oxychlorinating a hydrocarbon containing 1 to 4 carbon atoms, comprising conducting oxychlorination of said hydrocarbon containing 1 to 4 carbon atoms in the presence of the catalyst according to claim 1.

12. The process according to claim 11, wherein the hydrocarbon is ethylene and the oxychlorination produces 1,2-dichloroethane.

13. An alumina obtained by calcination at a temperature comprised between 700 and 950° C. of an alumina hydrate obtained as a by-product of only the ALFOL® linear primary alcohol process,
   wherein the ALFOL® linear primary alcohol process comprises:
   A. hydrogenation of triethylaluminum in the presence of aluminum metal, leading to hydrogenated diethylaluminum;
   B. ethylation of the hydrogenated diethylaluminum by adding ethylene, leading to triethylaluminum;
   C. growth reaction to build a mixture of higher molecular weight trialkylaluminums (called ethylene growth product) by further addition of ethylene to the triethylaluminum;
   D. oxidation of the ethylene growth product with air to the corresponding aluminum alkoxide; and
   E. hydrolysis of the aluminum alkoxide to a mixture of linear primary alcohols and an aqueous suspension of alumina hydrate.

14. An oxychlorination process comprising conducting oxychlorination in the presence of the catalyst according to claim 10.

15. An oxychlorination catalyst according to claim 1, wherein the oxychlorination catalyst does not show an apparent concentration increase for any of the active elements therein of more than 5% after use in an oxychlorination reaction for a period of time of one year.

16. The catalyst according to claim 1, wherein said calcination of said alumina hydrate is conducted at a temperature of 750-850° C.

17. The catalyst according to claim 1, further comprising two or three additional active elements, and wherein the active elements are selected from the following combinations: copper/magnesium/potassium, copper/magnesium/sodium; copper/magnesium/lithium, copper/magnesium/cesium, copper/magnesium/sodium/lithium, copper/magnesium/potassium/lithium and copper/magnesium/cesium/lithium, copper/magnesium/sodium/potassium, copper/magnesium/sodium/cesium and copper/magnesium/potassium/cesium.

18. The catalyst according to claim 1, further comprising two or three additional active elements, and wherein the active elements are selected from the following combinations: copper/magnesium/potassium, copper/magnesium/sodium; copper/magnesium/lithium, copper/magnesium/cesium, copper/magnesium/sodium/lithium, copper/magnesium/potassium/lithium and copper/magnesium/cesium/lithium.

19. The catalyst according to claim 1, wherein the copper content, calculated in metal form, is 30-90 g/kg of catalyst.

20. The catalyst according to claim 9, wherein the copper content, calculated in metal form, is 30-90 g/kg of catalyst, the magnesium content, calculated in metal form, is 10-30 g/kg of catalyst, and the alkali metal(s) content, calculated in metal form, is 0.1-30 g/kg of catalyst and wherein the Cu:Mg:alkali metal(s) atomic ratios are 1:0.1-2:0.05-2.

* * * * *